United States Patent [19]

Miyahara et al.

[11] Patent Number: 4,769,491

[45] Date of Patent: Sep. 6, 1988

[54] METHOD FOR PRODUCTION OF CYSTINE FROM CYSTEINE

[75] Investors: Shyoichiro Miyahara; Toshiaki Kamiguchi; Tooru Miyahara; Hashimukai Tadashi; Nitta Kazunari, all of Fukuoka, Japan

[73] Assignee: Mitsui Toatsu Chemicals, Inc., Tokyo, Japan

[21] Appl. No.: 49,807

[22] Filed: May 12, 1987

[51] Int. Cl.$^4$ ............................................. C07C 148/00
[52] U.S. Cl. ................................................... 562/557
[58] Field of Search ........................... 562/557; 568/26

[56] References Cited

U.S. PATENT DOCUMENTS

| 3,376,313 | 4/1968 | Wallace | 568/26 |
| 3,513,088 | 5/1970 | Karabinos | 568/26 |
| 3,948,922 | 4/1976 | Lowe | 568/60 |

FOREIGN PATENT DOCUMENTS

| 57-7634 | 2/1982 | Japan . | |
| 58-164566 | 9/1983 | Japan | 562/557 |

Primary Examiner—Michael L. Shippen
Attorney, Agent, or Firm—Browdy and Neimark

[57] ABSTRACT

From the aqueous solution containing cysteine obtained by the enzymatic method or fermentative method, cystine is produced in a high yield by oxidizing the cysteine in the presence of dimethyl sulfoxide.

2 Claims, No Drawings

METHOD FOR PRODUCTION OF CYSTINE FROM CYSTEINE

FIELD OF THE INVENTION

This invention relates to a method for the proudction of cystine by the oxidation of the cysteine obtained by the enzymatic method or the fermentative method.

L-cysteine and L-cystine are elementary S-containing amino acids which have found utility as medicines, raw materials for medicines, food additives, and additives for cosmetics. Particularly in recent years, the demand for these compounds as raw material for cold permanent wave liquid is growing steadily.

DESCRIPTION OF THE PRIOR ART

In the isolation of cysteine from the cysteine-containing reaction solution obtained by the fermentative method, the enzymatic method, the synthetic method, or any other method (hereinafter the term "reaction solution" shall mean the solution which exists after completion of the reaction of the enzymatic, fermentative, or synthetic method), since the composition of the reaction solution is complicated and the solubility of cysteine in water is very high, there have preveiled various methods which effect isolation and purification of cysteine by preliminarily causing the cysteine to react with a strong acid such as hydrochloric acid or p-toluene sulfonic acid thereby forming a corresponding salt.

These methods generally are complicated in procedure and afford cysteine in very low yields. It is difficult to remove the cysteine in a highly pure form from the reaction solution of complex composition obtained by the fermentative method. Particularly the isolation and purification of the cysteine from the reaction solution obtained by the fermentative or enzymatic method entails heavy loss because the reaction solution contains impurities originating in microorganisms.

Since cysteine is relatively liable to oxidation, there has been proposed a method which comprises forcibly oxidizing the cysteine in the reaction solution into cystine, separating the cystine in a purified form, and then electrolytically reducing the separated cystine thereby obtaining pure cysteine.

Several methods have been disclosed which effect oxidation of the cysteine in the cysteine fermentation broth. The method disclosed in the specification of Japanese Patent Publication No. SHO 57(1982)-7,634 accomplishes this oxidation using air or such peroxide as $H_2O_2$ with the pH value of the reaction mixture kept in the range of 5 to 10.

According to the inventors' tracing experiment, it is assumed that, in the method resorting to the oxidation with $H_2O_2$ or air, the reaction proceeds in the form of radical oxidation and entails drawbacks such as difficult control of the reaction conditions and occurrence of decompsoition products in a fairly large proportion.

When the reaction solution is a fermentation broth which contains in the cysteine reaction system such a metallic ion as $Fe^{++}$ or $Mn^{++}$ serving to catalyze the radical reaction as in the case of the method described above, cystine is obtained in a realtively high yield. The yield is poor, however, where the reaction solution contains virtually no metallic ion. If the added metallic ion such as $Fe^{++}$ or $Mn^{++}$ is mixed in the separated cystine, it has the possibility of producing adverse effects on the electrolytic reduction of cystine.

For the removal of used microorganic cells or used enzyme from the cysteine reaction solution obtained by the fermentative method or enzymatic method, the method has been found to be most effective which is carried out by adjusting the pH value of the reaction solution to a level of not more than 4 by the addition of HCl or $H_2SO_4$, adding activated carbon thereto, thermally treating the resultant solution thereby causing the used enzyme or used microorganic cells to be flocculated and adsorbed on the activated carbon, and subjecting the resultant composite to solid-liquid separation. In this case, the oxidation method using air or $H_2O_2$ requires that the reaction solution be kept at a pH of not less than 5 as specifically pointed out in the aforementioned specification and, therefore, $H_2O_2$ or air oxidation does not suit the oxidation of cysteine in an acidic condition after the treatment of the reaction solution.

Particularly by the inventors' tracing experiment, it has been confirmed that the oxidation with air effected under a strongly acidic condition in the neighborhood of pH 1 produces substantially no cystine.

Among the methods for the oxidation of cysteine heretofore known to the art are counted the method resorting to the oxidation with methyl xanthide (U.S. Pat. No. 4,039,586) and the method relying on irradiation with $\gamma$ ray (Chemical communication, 1968, 826–827). These methods, however, are not commercially feasible.

DESCRIPTION OF THE INVENTION

The inventors made a diligent study in search of a solution for the problems described above.

To be specific, this invention relates to a method for the production of cystine characterized by the steps of causing cytseine in the cysteine-containing aqueous solution obtained by the enzymatic method or fermentative method to be oxidized in the presence of dimethyl sulfoxide (this serves as an oxidizing agent) to thereby convert cysteine into cystine, and separating the resulting cystine.

The reaction solution subjected to the oxidation contemplated by the present invention has only to meet the requirement that it should be a cysteine-containing reaction solution obtained by the fermentative method or enzymatic method. For example, the reaction solution obtained by culturing an L-cysteine-producing microorganism such as of genus Pseudomonas using 2-aminothiazolin-4-carboxylic acid (ATC) as disclosed in the aforementioned specification of Japanese Patent Publication No. SHO 57(1982)-7,634 can be used. Desirably, this invention is applied to the reaction solution of a relatively high inorganic salt content originating in the process of cysteine production.

The inventors formerly developed and applied for patent a method for obtaining L-cysteine by using L-serine as a starting material and subjecting to enzymatic reaction using a sulfur-containing compound such as $Na_2S$, NaHS, or $H_2S$ destined to function as a sulfhydryl group-introducing agent in the presence of tryptophan synthase. The reaction solution obtained by this enzymatic reaction contains such inorganic salts as NaCl and $(NH_4)_2SO_4$.

When the method of this invention is applied to the enzymatic or fermentative reaction solution, the reaction velocity in the oxidation in the presence of dimethyl sulfoxide (hereinafter referred to briefly as "DMSO") tends to be increased by the catalytic action of the salt present in the oxidative reaction system presumably because the oxidation relies on ionic reaction.

This invention concerns a method for oxidizing the cysteine in the reaction solution obtained by the enzymatic method (hereinafter referred, inclusively of the fermentative method, to as "enzymatic method") into cystine. Since the reaction proceeds under mild conditions, it is not affected by the composition of the reaction solution.

The reaction solution, therefore, may contain an insignificant amount of the cystine formed in the course of the cysteine production and even contain the used enzyme or used microorganic cells originating in the culture. For example, the cysteine contained in the reaction solution which is freshly resulting from the enzymatic reaction and still containing the used enzyme or used microorganic cells may be oxidized into cystine by the addition of DMSO to the solution and removing the used enzyme or used microorganic cells from the solution thereby isolating the produced cystine.

As already described above, however, the removal of the used microorganic cells from the reaction solution in the present invention can be effected most effectively by the method which comprises thermally treating the reaction solution under an acidic condition of not more than pH 4, preferably in the neighborhood of pH 1 in the presence of an adsorbent thereby flocculating the used microorganic cells, causing the floccules to be adsorbed on the activated carbon, and eluting the adsorbate. To the acidic aqueous solution containing cysteine which results from removal of the used microorganic cells from the reaction solution as described above, DMSO is added to the solution as an oxidative reagent to thereby convert the cysteine into cystine. In the reaction for the oxidation of cysteine into cystine contemplated by the present invention, the reaction velocity increases in proportion as the ph value of the solution decreases and the yield of cystine increases in proportion as the acidity of the solution increases.

The amount of DMSO to be used is sufficient on the level of about 0.2 to 2.0 mols, preferably 0.5 to 1.0 mol, per mol of the cysteine contained in the reaction solution.

Though the temperature at which the reaction of this invention is to be carried out is not rigidly defined, it is desired to fall in the range of 5° C. to 100° C.

This invention does not require forced supply of oxygen to the reaction system. The reaction can be carried out in any conventional hermetically sealable reaction vessel, being possible even under an atomosphere of $N_2$ gas.

OPERATION AND EFFECT

Thus the oxidation is effected by the use of DMSO, and the present invention enjoys the following advantages.

(1) In the oxidation with air or the oxidation with $H_2O_2$, no proper reaction velocity can be obtained uless such a metal as $Fe^{++}$, $Mn^{++}$, or $Cu^{++}$ is added as a catalyst to the reaction system. The method of the present invention has absolutely no use for the catalyst.

Since the oxidation with air or the oxidation with $H_2O_2$ is a radical reaction, it does not terminate with the occurence of cystine but proceeds to the occurrence of such decomposition products as cysteic acid. As the result, the recovery of cystine inevitably entails heavy loss and the reaction of oxidation is not easily controlled. In the oxidation carried out in the presence of DMSO as contemplated in the present invention, since the oxidation is an ionic reaction, it proceeds moderately and produces cystine substantially quantitatively from cysteine. When the reaction is carried out in the presence of an electrolytic inorganic salt, the reaction velocity of the oxidation is increased. The effect of the presence of this electrolytic inorganic salt is particularly prominent when the method of this invention is applied to the L-cysteine reaction solution which is obtained by using L-serine as a substrate and effecting the enzymatic reaction of a sulfer-containing compound in the presence of tryptophane synthase.

(2) The aqueous cysteine solution to be subjected to the oxidation of this invention is desired to possess as low a pH value as possible. Where the aqueous cysteine solution resulting from the removal of the used microorganic cells, the removal being carried out using activated carbon under an acidic condition (pH 4 or less, is subjected to the oxidation reaction, the aqueous solution can be directly put to use in the oxidation reaction without requiring a treatment for pH adjustment.

As compared with the conventional method which resorts to the oxidation with air or the oxidation with $H_2O_2$, the method of the present invention which relies on the oxidation with DMSO brings about conspicuous effects such as lowered ratio of decomposition of cysteine into cysteic acid particularly under a strongly acidic condition. Data supporting this fact are shown in the following table.

In the test oxidation, an aqueous 10% L-cysteine solution was used as a model solution. DMSO and $H_2O_2$ were each used in an amount of 0.75 mol per mol of L-cysteine. In the case of the oxidation with air, air was passed through the solution at a rate of three times the volume of the solution per minute. In all the tests, the oxidation was carried out at room temperature for eight hours. In the table, the numerals in the upper bracket represent the conversions (oxidation ratios) of cysteine and those in the lower bracket the formation ratios of cystine (selectivities to cystine).

|     | DMSO  | Air   | $H_2O_2$ |
| --- | ----- | ----- | -------- |
| PH1 | 98/96 | 5/4   | 99/68    |
| PH7 | 87/85 | 85/79 | 99/76    |

Note
In the tests using air and $H_2O_2$, $FeCl_2$ was added in a minute amount to permit the presence of $Fe^{++}$ ion in the reaction system.

Now, the present invention will be described more specifically below with reference to working examples. In these working examples, cysteine and cystine were analyzed as follows. The analysis of cysteine was performed by the known Gaitonde method.

About 0.5 g of a given solution was taken as a sample, weighed accurately, and diluted with 2N HCl to 10 to 20 times the original volume. The diluted solution was further diluted with distilled water to about 100 times. The solution finally diluted to 1,000 to 2,000 times the original volume was colored with an acidic ninhydrin reagent and tested for absorbancy at 560 nm with an absorptiometer. Separately, standard samples of known concentrations were prepared in advance to obtain a calibration curve of the absorbancy at 560 nm. Then the cysteine concentration of the given solution was calculated from the calibration curve.

As regards the cystine concentration, a given solution diluted to 1000 to 2000 times the original volume as described above was mixed with a roughly equal volume of a 5-μM 1,4-dithiothreitol (reducing agent), adjusted to pH 8.0 to 8.5 by the addition of 2N NaOH, and left standing at room temperature for one hour for thorough reducing of cystine into cysteine to permit calculation the cysteine concentration by the method described above. The cystine concentration was found by deducting the cysteine concentration before the reduction from the concentration so calculated.

EXAMPLE 1

In a separable flask having an inner volume of 300 ml and fitted with a stirrer, 91 g of an aqueous L-serine solution containing 22.0 wt % of L-serine (0.19 mol as L-serine), 28.1 g of sodium hydrosulfide dihydrate (NaSH·2H$_2$O) (0.38 mol), and 10 g of a culture broth of tryptophan synthase originating from *Escherichia coli* MT-10242 (FERM BP- 20) and still containing the used cells (dry content 2.2 g), were combined, adjusted to pH 7.5 by the addition of an aqueous 5% sodium hydroxide solution, and diluted with water to a total volume of 200 ml. The resultant mixture was placed in a constant temperature bath at 35° C. and left reacting therein for 24 hours.

After completion of the reaction, the reaction mixture was adjusted to pH 1.0 with hydrochloric acid, then combined with 5 g of activated carbon (produced by Takeda Chemical Industries, Ltd. and marketed under trademark designation of "Tokusei Shirasagi"), and heated at 80° C. for 30 minutes. After this heat treatment, the reaction mixture kept at 80° C. was hot filtered through a buchner funnel to remove used microorganic cells and obtain 188 g of a reaction filtrate in a treated form. This reaction filtrate was found by analysis to contain 20.1 g (0.166 mol) of L-cysteine and 2.0 g (0.008 mol) of L-cystine both reduces as L-cysteine. The conversion of L-serine to L-cysteine and L-cysteine was found by calculated to be 95.8%.

The reaction solution thus obtained by the heat treatment was transferred into a separable flask having an inner volume of 300 ml and fitted with a stirrer and stirred therein with 9.7 g of DMSO at room temperature for eight hours to obtain 196.2 g of a solution having L-cystine crystals precipitated therein (the solution had still pH 1). In this solution, 0.2 g of L-cysteine remained.

The solution resulting from the oxidation was neutralized to about pH 5 by the addition of an aqueous 5% sodium hydroxide solution to induce precipitation of crystals. The crystals were separated by filtration and dried to obtain 19.8 g (0.165 mol as 100%) of white powdery crystals. These crystals were found to possess a refractive index, $[\alpha]_D^{20} = -218°$ (C=2, 2N HCl), an Fe content of not more than 10 ppm, and a purity of not less than 98.5%. As regards the ratio of recovery, 95.0% of all the L-cysteine and L-cystine present in the reaction solution were recovered. The ratio of decomposition was not more than 2%.

Comparative Experiment

The same reaction solution obtained by following the procedure of Example 1 was heat treated and then neutralized with an aqueous 5% sodium hydroxide solution to about pH 5. The reaction solution resulting from this heat treatment was transferred into the same separable flask having an inner volume of 300 ml as used in Example 1, mixed therein with 0.2 g of FeCl$_2$ and blown with air introduced at a flow rate of about 200 ml/min. at room temperature, to produce 200.8 g of a solution having L-cystine crystals precipitated therein. In the soluion, 4.2 g of L-cysteine remained.

By separating the crystals from the reaction solution through filtration and drying the separated crystals, there was obtained 14.8 g of white powdery crystals. The crystals were found to possess a refractive index, $[\alpha]_D^{20} = -215°$ (C=2, 2N HCl), a Fe content of 30 ppm, and a purity of not less than 98.5%. As regards the ratio of recovery, 70.3% of all L-cysteine and L-cystine present in the reaction solution were recovered. The ratio of decomposition was 9.9%.

EXAMPLE 2

In a separable flask having an inner volume of 300 ml and fitted with a stirrer, 91 g of an aqueous L-serine solution containing 22.0 wt% of L-serine (0.19 mol of L-serine), 28.1 g (0.38 mol) of sodium hydrosulfide dihydrate (NaSH·2H$_2$O), and 10 g of a culture broth of tryptophan synthase originating from *Escherichia coli* MT-10242 (FERM BP-20) and still containing the used cells (dry content 2.2 g), were combined, adjusted to pH 7.5 by the addition of an aqueous 5% sodium hydroxide solution and then diluted with water to a total volume of 200 ml. The diluted solution was placed in a constant temperature bath at 35° C. and left reacting therein for 24 hours.

The reaction solution obtained after completion of the reaction was found by analysis to cotnain 18.5 g (0.153 mol) of L-cystein and 3.2 g (0.013 mol) of L-cystine both reduced as L-cysteine. The conversion of L-serine to L-cysteine and L-cystine was calculated to be 94.2%.

The reaction solution consequently obtained was adjusted to pH 0.5 by the addition of about 30 ml of concentrated hydrochloric acid and combined with 0.97 g of DMSO and stirred at 35° C. for eight hours for oxidation. At this stage, the oxidized solution contained 0.7 g (0.006 mol) of L-systeine and 20.7 g (0.086 mol) of L-cystine. The conversion of L-serine to L-cystine was calculated to be 90.6%.

The oxidized solution and 5 g of activated carbon (product of Takeda Chemical Industries, Ltd.) added thereto were heated at 80° C. for 30 minutes. The resultant reaction mixture kept at 80° C. was hot filtered through a Buchner funnel to remove used microorganic cells and obtain 2.30 g of a homogeneous filtrate (having still pH 0.5) in a treated form, This filtrate was found by analysis to contain 0.3 g (0.002 mol) of L-cysteine and 20.8 g (0.087 mol) of L-cystine. The conversion from L-serine to L-cystine was found to be 91.3%.

The solution resulting from the separation of the used microorganic cells was neutralized to pH 2 by dropwise addition of about 5 ml of 30% NaOH solution to induce precipitation of L-cystine crsytals. The crystals were separated by vacuum filtration with a buchner funnel, washed thoroughly with 50 ml of water, and dried to afford 20.2 g (0.084 mol as 100%) of white powdery crystals. These crystals were found to possess a refractive index, $[\alpha]_D^{20} = -218.6$ (C=2, 2N HCl), a Fe content of not more than 10 ppm, and purity of not less than 98.5%. As regards the ratio of recovery, nearly 100% of all L-cysteine and L-cystine present in the reaction solution were recoverd.

What is claimed is:

1. A method for the production of cystine, which comprises oxidizing cysteine in a cysteine-containing aqueous solution having a pH value of not more than 4, said solution having been obtained by an enzymatic method or fermentative method, in the presence of dimethyl sulfoxide employed as an oxidizing agent, thereby converting said cysteine into cystine; and separating the cystine.

2. A method according to claim 1, wherein said cysteine-containing aqueous solution is an aqueous L-cysteine solution obtained by the reaction of L-serine with a sulfhydryl group-containing compound in the presence of tryptophan synthase.